United States Patent [19]

Kuehn

[11] 4,139,577

[45] Feb. 13, 1979

[54] POLYMERIZABLE COMPOSITION COMPRISING A TETRACARBOXYLIC ESTER MONOMER USEFUL FOR IMPARTING FLAME RETARDANCE TO RESIN POLYMERS

[75] Inventor: Erich Kuehn, Wilmington, Del.

[73] Assignee: ICI Americas Inc., Wilmington, Del.

[21] Appl. No.: 748,170

[22] Filed: Dec. 7, 1976

[51] Int. Cl.² .......................... C08L 67/06; C09K 3/28
[52] U.S. Cl. .................................... 260/871; 260/40 R; 260/40 TN; 260/859 R; 260/861; 260/862; 260/863; 260/867; 260/868; 526/284; 526/292
[58] Field of Search ................ 526/284, 292; 260/861, 260/895, 871; 560/80

[56] References Cited

U.S. PATENT DOCUMENTS

| | | | |
|---|---|---|---|
| 3,836,606 | 9/1974 | Baum | 260/861 |
| 3,860,555 | 1/1975 | Chretien et al. | 260/861 |
| 3,954,840 | 5/1976 | Yamashita et al. | 560/80 |

FOREIGN PATENT DOCUMENTS 2411169  9/1974  Fed. Rep. of Germany ........... 526/284

*Primary Examiner*—Allan Lieberman
*Attorney, Agent, or Firm*—Richard A. Rowe; Roger R. Horton; Jay W. Sanner

[57] ABSTRACT

Esters of tetracarboxylic acids having the following general formula:

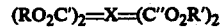

wherein =X= is selected from tetravalent 5 or 6 membered or a double 6 membered ring system and wherein C' and C" carbons are attached to separate pairs of vicinal carbons and R and R' are selected from halogenated organic radicals containing a least 2 atoms of chlorine or bromine and the other of each R and R' is selected from —H, —CH$_2$CH(OH)C-H$_2$O$_2$CCR"=CH$_2$, and —CH[CH$_2$(OH)]C-H$_2$O$_2$CCR"=CH$_2$ are useful in the preparations of high molecular weight polymers and copolymers which are improved in fire retardance and strength.

6 Claims, No Drawings

POLYMERIZABLE COMPOSITION COMPRISING A TETRACARBOXYLIC ESTER MONOMER USEFUL FOR IMPARTING FLAME RETARDANCE TO RESIN POLYMERS

The invention relates to esters of tetracarboxylic acids and highly branched resins made therefrom having exceptional fire retardance and strength. In particular, the esters include reaction products of dianhydrides with monohydroxy halogenated compounds or their equivalent monohydroxy ethylenically unsaturated compounds which have been brominated or chlorinated afterward. In addition they include partial esters which have been further reacted with ethylenically unsaturated epoxy compounds.

The tetracarboxylic esters are selected from a group consisting of those having the general formula:

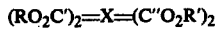

$$(RO_2C')_2{=}X{=}(C''O_2R')_2$$

wherein $=X=$ is selected from a tetravalent 5 or 6 membered single ringed system or a double 6 membered ring system wherein the C' carbons are attached to a pair of vicinal carbons in said ring system and the C'' carbons are attached to another pair of vicinal carbons in said ring system, wherein one each of R and R' is a halogenated organic radical having at least 2 carbon atoms and at least 2 atoms of chlorine or bromine and the other of each R and R' is selected from —H, —CH$_2$CH(OH)CH$_2$O$_2$CCR''=CH$_2$, and —CH[CH$_2$(OH)]CH$_2$O$_2$CCR''=CH$_2$ wherein R'' is —H or —CH$_3$.

Unsaturated esters of anhydrides and dianhydrides have been known and employed in the manufacture of resins as, for example, those described in U.S. Pat. Nos. 3,046,258; 3,225,065; 3,336,360; 3,391,223; 3,451,980; 3,535,404; 3,652,598; 3,760,033; 3,785,849; 3,905,942 and 3,919,172. In addition, similar halogenated compounds have been described such as in U.S. Pat. Nos. 3,507,933, 3,748,303, 3,394,204 and 3,438,946. Also to be considered are compositions described in my copending application U.S. Ser. No. 727,411, now U.S. Pat. No. 4,095,601.

The esters in the above-described formula may be homopolymerized or copolymerized with additional monomers or resins to form high molecular weight addition or condensation type resins which are improved in strength and fire retardance.

These monomers are prepared in one or two steps by first reacting a dianhydride having a general formula O(OC')$_2$=X=(C''O)$_2$O with a monohydroxy halogenated organic compound in mol ratios of dianhydride to halogenated compound o about 0.5 to form a halogenated di-half-ester which optionally may be reacted with an ethylenically unsaturated glycidyl compound in a second step in molar ratios of di-half-ester/glycidyl compound of 0.5-1 to form the hydroxyl-containing tri- or tetraester. Alternatively, they may be made by reacting in the first step a monohydroxy ethylenically unsaturated compound in similar proportions and thereafter halogenating the unsaturation with chlorine or bromine prior to the second reaction step.

The tetrafunctional dianhydride may be selected from compounds wherein the $=X=$ in the above general formula is selected from a tetravalent 5 or 6 membered carbocyclic or heterocyclic single-ringed system or a double 6 membered ring system. Usually the tetracarboxylic acids occur as two pairs of carboxyl groups on separate pairs of adjacent carbon atoms. Each pair of carboxyl groups may occur on the same, adjacent rings or separate rings. The ring systems may be selected from carbocyclic or heterocyclic systems which contain elements such as nitrogen and oxygen, for example, pyrrole and furan, pyridine, etc.

Representative of 5 membered ring systems are derivatives of cyclopentane, tetrahydrofuran, pyrrole, cyclopentene, cyclopentadiene and furan. Representative of 6 membered ring systems are benzene, pyridine, pyran, cyclohexane, napthalene, benzophenone, dioxane, dibenzene, anthracene, and dibenzyl methane. Representative dianhydrides are: tetrahydrofuran tetracarboxylic dianhydride; cyclopentane tetracarboxylic dianhydride; pyromellitic dianhydride; benzophenone tetracarboxylic dianhydride; naphthalene tetracarboxylic dianhydride; pyrrolene tetracarboxylic dianhydride; anthracene tetracarboxylic dianhydride, biphenyl tetracarboxylic dianhydride; diphenylmethane tetracarboxylic dianhydride. Also included are halogenated and alkylated derivatives of the tetracarboxylic dianhydrides such as 2,2-bis(3,4-dicarboxyphenyl)hexafluopropane dianhydride.

The monohydroxy compounds useful in preparing ester groups which provide halogenated ethylenically unsaturated organic radicals are alcohols such as allyl alcohol, glycerol diallyl ether, trimethylolpropane diallyl ether, monohydroxy ethyl-butene-2,3-alcohol, monoacrylic or monomethacrylic esters of dihydroxy compounds, and alkoxylated derivatives of these monohydroxy esters.

Preferred monohydroxy unsaturated compounds which may be employed in the fist stage reactions include any hydroxyalkyl acrylate of the formula HOR'O$_2$CCR''=CH$_2$ where R' is a divalent alkyl radical having 1-3 carbon atoms and R'' is —H or —CH$_3$. Specific examples of such compounds include hydroxymethyl, hydroxyethyl and hydroxyisopropylacrylate, hydroxymethyl, hydroxyethyl and hydroxyisopropyl methacrylate. Furthermore, these and the above-described monohydroxy compounds may be chlorinated or brominated to form the halogenated derivative prior to their addition to the dianhydride.

Many monohydroxy halogenated aliphatic and arylaliphatic compounds are available commercially. Such materials having at least 2 carbon atoms, 1 hydroxyl group and at least 2 atoms of chlorine or bromine and a carbon/halogen atomic ratio of 1-5 are preferred. Such materials include di-, tri- and tetrahalogenated ethanol, propanol, isopropanol, butanol, isobutanol, pentanol, isopentanol, neopentanol and halogenated aromatic alcohols.

The glycidyl compound is selected from glycidyl acrylate and glycidyl methacrylate, and depending upon the ring opening sequence the ester group formed upon condensation with the free carboxyl group will have the structure —CH$_2$CH(OH)CH$_2$O$_2$CCR''C=CH$_2$ or —CH(CH$_2$OH)CH$_2$O$_2$CCR''=CH$_2$ wherein R'' is —H or —CH$_3$. It is not known to what extent the free hydroxyl group formed participates in further condensation.

As previously stated, the process for preparing the ester monomers of this invention is basically a two-stage process. The first stage is conducted by mixing the dianhydride and the halogenated monohydroxy compound in a reaction vessel to open the anhydride rings to form a di-half-diester. This reaction is carried out over a wide range of temperatures as low as room temperature but preferably between 70 and 120° C., although temperatures as high as 150° C. or higher may be employed depending upon the stability of the reactants or the acceptability of lower yields due to side reactions. To obtain maximum conversion to the di-half-diester a mol ratio of dianhydride to the monohydroxy halogenated derivative of 0.5 is desirable. Slight molar excesses or deficiencies of the hydroxy compound do not substantially affect the resins made therefrom.

The reaction may be carried out in bulk or, if desired, in the presence of an inert aromatic or polar solvent such as, for example, dimethylformamide, a polyethylene glycol dimethyl ether, ketones, toluenes, xylene, and in many instances the vinyl monomer such as styrene, methyl methacrylate, etc.

The first stage of the reaction is usually conducted in the absence of a catalyst; however, if desired a catalyst for anhydride ring opening may be employed, such as the organic amine complexes of iron, copper or nickel.

An alternative procedure for preparing the halogenated di-half-diester is to halogenate a product formed by reacting monohydroxy unsaturated compounds in similar mol ratios with the dianhydride. This halogenation step is carried out by any well-known technique wherein the addition of bromine or chlorine to the ethylenically unsaturated ester is not de-esterified. Usually the reaction is carried out at temperatures below 20° C. in the presence of an inert solvent.

The optional second stage reaction may be conducted by adding 1 or 2 mols of the glycidyl compound to the product of the first stage reaction. The temperature at which the second stage reaction is conducted is subject to wide variation. It can be carried out at various temperatures ranging from room temperature to about 150° C. Since the reaction is usually exothermic, it is necessary to control the addition rate such that the temperature does not exceed about 150° C. as a means for minimizing side reactions.

While the use of a catalyst is not essential in the second stage reaction, it may be desirable to employ an amine catalyst such as N-methylmorpholine.

Since the process has at least 1 reactant in each step containing polymerizable ethylenic unsaturation it is desirable, although not absolutely necessary, to employ an inhibitor in the reaction mixture, for example a quinone, a hydroquinone, or a phenolic inhibitor of the type conventionally employed with unsaturated acrylic type monomers. Further examples of inhibitors include quinone, hydroquinone, methylquinone, methylhydroquinone and the dimethyl ether of hydroquinone.

The di-, tri- and tetra- esters of the dianhydrides described above, because they contain on the average of 2 active hydrogens either 2 hydroxyl, 1 hydroxyl and 1 carboxyl hydrogen, or 2 carboxyl are useful in the formation of condensation product resins. They are also useful as intermediates in the formation of free radical addition polymers because of their 2, 3 or 4 ethylene groups.

It is, therefore, the object of the present invention to provide new monomers for use in forming polyester condensation type resins as well as addition copolymer resins. Furthermore, the invention includes polymerizable combination of these monomers as well as sheets, adhesives and laminates made therefrom.

Suitable comonomers are ethylenically unsaturated monomers especially styrene, divinyl benzene and vinyl toluene which act as solvents for the unsaturated esters and which are capable of undergoing addition reactions in the presence of a suitable initiator catalyst. These monomers usually form relatively high molecular weight cross-linked highly branched resins in a short period of time with the use of appropriate catalysts.

Reactions between the unsaturated esters and other ethylenically unsaturated monomers or resins can be carried out at substantially ambient temperature when initiated by means of ultraviolet light, by means of chemical initiators/activator systems or by means of high energy electrons. The curing is usually effected in the presence of a free radical initiator type catalyst such as an organic peroxygen compound, for example, benzoyl peroxide, tertiary butyl hydroperoxide, ditertiary butyl peroxide, dicumyl peroxide, tertiary butyl peracetate, tertiary butyl perbenzoate, ditertiary butyl perphthalate, tertiary butyl peroxyisopropyl carbonate or bisisobutyronitrile. The activators or catalysts can be employed in amounts of from 0.01 to about 5% by weight of the monomers. Photosensitive catalysts may include, for example, inorganic uranyl salts such as uranyl nitrate, uranyl chloride, uranyl salts of organic acids, photosensitive dyes such as rose bengal, and aromatic disulfides such as diphenyl disulfide. Other photosensitizers include alpha diketones, such as biacetyl, benzyl, benzophenone, benzoin and the like. Such systems require the presence of a reducing agent capable of reducing the photo-sensitizer the most common of which are amines, such as propyl amine, dipropyl amine, and the like.

The comonomers from which an addition copolymer is derived may be, for example, a vinyl ester, an aryl vinyl compound, or a vinyl nitrile. If desired, the vinyl copolymer may be derived from a plurality of vinyl monomers. Suitable vinyl esters include, for example, vinyl acetate, and esters of acrylic acid and methacrylic acid wherein the ester moiety is an alkyl, aryl, alkaryl, aralkyl or cycloalkyl group. Vinyl esters of acrylic and methacrylic acids may also be employed.

Aromatic vinyl compounds such as styrene or an alpha alkyl derivative thereof, for example alpha-methyl styrene or vinyl naphthalene, are readily available commercially.

Suitable vinyl nitriles include, for example, acrylonitrile and derivatives thereof, for example methacrylonitrile.

The unsaturated esters of the dianhydride of the invention may also be directly copolymerized with ethylenically unsaturated polyesters which are formed by the reaction of ethylenically unsaturated polycarboxylic acids and polyols.

Ethylenically unsaturated polyester resins are well known in the art and are usually prepared by reacting carboxylic acids or their anhydrides with polyhydric alcohols. They are prepared using a procedure wherein at least one of the reactive components contains alpha,-beta-ethylenic unsaturation. These resins while primarily linear can contain branch chains by the addition of polyols or polycarboxylic acids having more than two functional groups. Usually they contain a plurality of ethylenically unsaturated linkages distributed along the backbones of their polymer chains. The use of alpha,-beta-ethylenically unsaturated polycarboxylic acids provides a convenient method of introducing ethylenic unsaturation into the polyester resin. It is preferred to employ alpha,beta-ethylenically unsaturated dicarboxylic acids such as maleic, fumaric, citraconic, gammic, gamma-dimethyl citraconic, mezaconic, itaconic, alpha methyl itaconic, gamma-methyl itaconic, tetraconic, and the like, as well as mixtures thereof, but minor amounts of alpha,beta-ethylenically unsaturated polycarboxylic acids containing three or more carboxylic groups such as aconitic acid and the like together with the dicarboxylic acids are also useful.

Whenever available, the anhydrides of any of the afore-mentioned alpha,beta-ethylenically unsaturated polycarboxylic acids may be substituted for the acid. In addition, suitable saturated acids or their anhydrides, when available, which may also be incorporated along with the unsaturated polyesters include, for example, phthalic acid or anhydride, isophthalic acid, terephthalic acid, tetrabromophthalic acid, tetrachlorophthalic acid, adipic acid, sebacic acid, glutaric acid, or mixtures thereof. Of particular interest may be mentioned a mixture of isophthalic or orthophthalic acid and fumaric/maleic acids.

Any of a large number of ethylenically unsaturated or saturated polyhydric alcohols may be employed with any of the above suitable mixtures. Dihydric alcohols and especially saturated aliphatic diols are preferred as coreactants in the preparation of polyester resins. Among the dihydric alcohols which may be employed are saturated aliphatic diols such as ethylene glycol, propylene glycol, butylene glycol, diethylene glycol, dipropylene glycol, triethylene glycol, tetraethylene glycol, butane diol, pentane diol, hexane diol, neopentyl glycol, and the like as well as mixtures thereof. Among the polyols having more than two hydroxyl groups which may be employed in minor amounts to form branch chains are saturated aliphatic polyols such as glycerol, trimethylolethane, trimethylolpropane, pentaerythritol, arabitol, xylitol, dulcitol, sorbitol, mannitol and the like as well as mixtures thereof. In addition, aliphatic aromatic diols and polyols may be employed as well as halogenated and alkoxylated derivatives thereof such as alkoxylated bisphenol A.

Other ethylenically unsaturated materials may be copolymerized such as vinyl ester urethane resins as disclosed in U.S. Pat. Nos. 3,876,726; 3,297,745; 3,371,056; 3,509,234; 3,641,199; 3,642,943; and 3,677,920, to name a few.

The ethylenically unsaturated polyester may also include typical ethylenically unsaturated polyepoxy condenstion products, or polyethers produced as, for example, those formed from epichlorohydrin and diols such as bisphenol A, and their ethylenically unsaturated condensation products. Epoxidized polybutadienes are also useful.

The ethylenically unsaturated polymer material may also contain polyisocyanurates such as poly(1,3,5-tri-R substituted S-triazine-2,4,6 trione) wherein the R group may contain ethylenic unsaturation or groups reactive with ethylenically unsaturated materials. R groups may also be linked with epoxy, polyurethane and polyester resins. Such isocyanurates are represented by U.S. Pat. Nos. 2,952,655; 3,041,313; 3,821,098; 3,850,770; 3,719,638; 3,437,500; 3,947,736; and 3,762,269.

The following examples illustrate ways in which the invention has been carried out but are not to be construed as limiting its scope.

EXAMPLE 1

The di-half-ester formed by reacting 2 mols of tribromoneopentyl alcohol with 1 mol of 3,3',4,4'benzophenone tetracarboxylic dianhydride is prepared as follows: In a 2 liter reaction flask equipped with stirrer, nitrogen inlet, condenser, and thermometer is placed 1,169.4 grams of tribromoneopentyl alcohol and melted by heating to 65° C. Thereafter 579.6 grams of benzophenone tetracarboxylic dianhydride is added with further heating and stirring until the mixture is clear at 150° C. This mixture is held at a range of 140°-160° C. for 1 hour and is then poured into an aluminum tray to cool. The clear, amber solid which results has a softening point of 96° C., and an acid value of 118 (theoretical, 115.4).

A polyester resin is made by condensing the di-half-ester described above with fumaric acid and polyoxypropylene(2)tetrabromo bisphenol A as follows: Into a 500 ml. flask equipped with stirrer, nitrogen inlet, thermometer, and reflux condenser is mixed 270.8 grams of polyoxypropylene(2)tetrabromo bisphenol A, 116.6 grams of the above di-half-ester, and 32.5 grams fumaric acid along with 0.21 grams hydroquinone. This mixture is heated to about 125° C. whereupon the mixture becomes clear. The first water of condensation is distilled off at about 186° C. The temperature is gradually increased to 200° C. and after about 4 hours, a clear, amber resin results which has an acid value of 27.9 and a ball and ring softening point of 123° C.

This material is then dissolved in styrene to form a 60 percent by weight resin solids in styrene solution which has a viscosity of 492 centipoises at room temperature.

A 2-ply fiber glass laminate is then prepared by first mixing 450 grams of the resin/styrene solution, 4.5 grams 6 percent cobalt naphthanate, 7.2 grams methyl ethyl ketone peroxide containing 40 percent dimethyl phthalate, 0.9 grams dimethyl aniline, 1.8 grams tertiary butyl catechol (10 percent solution in styrene), and working the resin into the fiber glass as follows: A sheet of polyester film is placed on a flat surface, a 4.5 gram sheet of C-glass surfacing veil is placed on the film followed by 2 chopped glass mats weighing 121 grams. Resin is poured over the glass to wet the glass and thereafter another sheet of C-glass surfacing veil weighing 4.5 grams and a top sheet of polyester film is placed over the wetted laminate. Air bubbles are worked out of the resin by pressing and smoothing. After a 24 hr. cure at room temperature, and 4 hrs. at 100° C., the clear, strong laminate possesses strength characteristics found in Table I.

EXAMPLE 2

A laminate as described in Example 1 is prepared by first mixing 435 grams of the 60 percent solids/styrene solution of Example 1, 21.75 grams antimony trioxide, 6.96 grams methyl ethyl ketone peroxide in 40 percent dimethylphthalate, 4.3 grams 6 percent cobalt naphthanate, 0.87 grams dimethyl aniline, 1.74 grams 10 percent tertiary butyl catechol and pouring this mix over 2 sheets of chopped glass mat weighing 123 grams, and two 4.5 gram sheets of C-glass surfacing veil as described in Example 1. After a 24 hr. cure at room temperature and a post-cure of 4 hrs. at 100° C. the laminate was subjected to physical tests, the results of which are found in Table I.

EXAMPLE 3

A polyester resin condensate is prepared by mixing dibromoneopentyl glycol, the dicarboxylic acid prepared in Example 1, and fumaric acid in molar portions of 1.025/0.5/0.5 respectively. This is accomplished by mixing in a 500 ml. flask equipped as described in Example 1, 122.2 grams dibromoneopentyl glycol, 221.2 grams of the diacid of Example 1, and 26.4 grams fumaric acid, and 0.18 grams hydroquinone. The condensation is carried out at 200° C. to remove by-product water. The resultant resin is poured into an aluminum tray, permitted to cool, and forms a solid amber colored resin having an acid value of 27.11.

EXAMPLE 4

A dicarboxylic acid is prepared by reacting 1 mol of tetrahydrofuran-2,3,4,5-tetracarboxylic dianhydride with 2 mols of tribromoneopentyl alcohol accordingly: Into a flask described previously, is charged 339.25 grams tribromoneopentyl alcohol and 110.74 grams of the dianhydride which is added slowly so that a temperature of 175° C. is not exceeded. The reaction mass is then cooled to 150° C. and held for 1 hr., and thereafter poured into an aluminum tray. The resin which results is clear and has an amber color, a softening point of 83° C. and an acid value of 130.8 (theoretical, 130.19).

EXAMPLE 5

The diacid of Example 4 is used to prepare a polyester resin by condensing it with polyoxypropylene(2)tetrabromo bisphenol A in admixture with fumaric acid in molar ratios of 1.03/0.3/0.7, diol/diacid/fumaric acid. This is accomplished by mixing 332.5 grams of the diol, 127.5 grams diacid of Example 4 and 39.5 grams fumaric acid and 0.25 grams of hydroquinone and heating for 4 hrs., at 200° C. The resulting amber colored polyester resin has an acid value ranging from 27.95–29.35 and a softening temperature of about 120° C.

60 parts of the resin is dissolved with 40 parts styrene to make a 60 percent solids solution.

2-ply laminates are prepared by first mixing 420 grams of the 60 percent resin solution with 3.36 grams cobalt naphthanate (6% cobalt), 6.72 grams methyl ethyl ketone peroxide in 40 percent dimethylphthalate, 0.84 grams tertiary butyl catechol and 1.68 grams of dimethyl aniline and laminates prepared as in Example 1 using chopped fiber glass weighing 118 grams and 2 layers of C-glass surfacing veil weighing 9 grams. The resin exhibits excellent glass wet-out and after a room temperature cure of 24 hrs. and a 100 ° C. cure for 4 hrs., the clear, amber laminate exhibits excellent physical properties as shown in Table I.

Another laminate is prepared as described in the above paragraph with the addition of 5 percent antimony oxide ($Sb_2O_3$). Physical properties for this laminate are shown in Table I.

EXAMPLE 6

A diacid is prepared by reacting 1 mol of pyromelliticdianhydride with 2 mols of 2,3-dibromopropanol by mixing 299 grams of the propanol with 150 grams of the dianhydride. The mixture is then heated for 4 hrs. at 160° and poured into an aluminum tray to cool.

EXAMPLE 7

A polyester resin condensate is prepared by condensing 0.2 mols of the diacid of Example 6 with 1 mol of bis 2-hydroxyethylamino-octachlorobiphenyl and 0.8 mols of maleic anhydride employing procedures similar to that disclosed for previous resin condensates.

EXAMPLE 8

A polyester resin is made by condensing a mixture containing 0.5 mols of the diacid from Example 1, 0.5 mols of fumaric acid and 1.03 mols of polyoxypropylene(2)tetrabromo bisphenol A in the presence of hydroquinone. The mixture is heated at 150°–190° C. and held at that temperature for 5 hrs., and thereafter poured into an aluminum tray to cool. The resulting resin has an acid value of 32.56 and a ball and ring softening point of 123° C. A 60 percent solid resin in styrene solution is prepared and employed in fabricating a laminate as described in Example 1. The physical properties are shown in Table I and compared with one containing 5 percent antimony trioxide.

EXAMPLE 9

A polyester resin condensate is prepared by mixing 0.5 mols of the diacid from Example 1, 0.5 mols fumaric acid, and 1.03 mols of dibromoneopentyl glycol and heating according to the procedure of Example 8. The resultant resin has an acid value of 33.37 and a softening point of 118° C.

EXAMPLE 10

The reaction is carried out between 1 mol of tetrahydrofuran 2,3,4,5-tetracarboxylic dianhydride with 2 molar portions of hydroxyethyl methacrylate as follows: Into a 1 liter flask equipped as previously described is charged 114.57 grams of hydroxyethyl methacrylate, 86.5 grams of tetrahydrofuran dianhydride and 0.22 grams of hydroquinone. This mixture is heated to 120° C. and held at this temperature for about 1 hr. prior to the addition of 200 grams of methylene chloride, after which the contents of the flask is cooled to 8° C. in an ice water bath. The bromination of this product with 2 mols of bromine is carried out by adding 130 grams of bromine drop-wise over a 2 hr. period at a rate such that the heat of exotherm does not raise the temperature above 18° C. The methylene chloride is then removed under vacuum after which the contents are heated to 83° C. and combined with 119.56 grams of glycidyl methacrylate which are added drop-wise over a 1 hr. period such that the heat of exotherm does not cause the contents to rise above 133° C. The contents are then stirred and mixed with 121 grams of styrene at 125° for 1 hr. to yield a highly viscous resin. The clear, amber solution has a viscosity in the range of 518 centipoises at room temperature.

EXAMPLE 11

1 molar portion of tetrahydrofuran 2,3,4,5-tetracarboxylic dianhydride and 2 molar portions of tribromoneopentyl alcohol are reacted to form a diacid. This diacid is then reacted with 2 molar portions of glycidyl methacrylate according to the following procedure: 909.56 grams of tribromoneopentyl alcohol are melted at 82° C. and thereafter mixed with 296.96 grams of tetrahydrofuran dianhydride and 0.81 grams of hydroquinone. The mixture is held at 130°–164° C. for 45 min. and thereafter lowered to 120° C. at which time 410.44 grams of glycidyl methacrylate are added drop-wise over a 1 hr. period such that the exothermic heat does not cause the temperature of the reactants to exceed 135° C. After a 2 hr. holding period at 120° C. the clear, amber viscous resin has an acid value of 3.96. The remaining resin is dissolved in 586 grams of styrene and cooled to room temperature after which the viscosity of the clear amber solution is 714 centipoises.

Laminates are prepared from this styrene solution according to Example 1 with and without antimony oxide. Physical properties are listed in Table I.

EXAMPLE 12

A reaction product of 1 molar quantity of 3,3',4,4'-benzophenone tetracarboxylic dianhydride with 2 molar portions of tribromoneopentyl alcohol and 2 molar portions of glycidyl methacrylate are made by first condensing 415.5 grams of tribromoneopentyl alcohol and 205.9 grams of the dianhydride at 133°-140° C. for 1 hr. Thereafter the temperature is dropped to 133° C. whereafter 0.4 grams of hydroquinone and 187.5 grams of glycidyl methacrylate is added drop-wise over a period of 1 hr. such that the heat of exotherm does not heat the reactants above 140° C.

To this warm resin solution is added 268 grams of styrene. When cooled to room temperature, the solution has a viscosity of 664 centipoises.

This styrene solution is employed to produce laminates as described in Example 1 and exhibits properties as shown in Table I.

EXAMPLE 13

A reaction product of 1 molar portion of pyromellitic dianhydride with 2 molar portions of a monoester formed by reacting equimolar portions of methacrylic acid and polyoxypropylene(2)tetrabromo bisphenol A is first made and thereafter brominated. This brominated diacid is then further reacted with 2 molar portions of glycidyl methacrylate according to the following procedure: 383.4 grams of polyoxypropylene(2)tetrabromo bisphenol A monomethacrylate is melted at a temperature of about 80° C. after which 57.42 grams of pyromellitic dianhydride are added. The mixture is then further heated to 170° C. and held for 1 hr. After cooling to 130° C., 300 grams of methylene chloride are added as solvent. The flask is then cooled in an ice bath to about 10° C. and thereafter 84.24 grams of bromine are added over a period of 1 hr. such that the temperature of the reactants does not exceed 10°-15° C. The methylene chloride is thereafter removed under vacuum distillation and the mixture heated to 130° C. 81.31 grams of commercial grade glycidyl methacrylate is added within a 30 min. period and thereafter the temperature is held at 135° C. for 1 hr. The resin resulting is poured into a tray and cooled. This resin can be dissolved in styrene to form solutions similar to those described in previous Examples to make laminates.

EXAMPLE 14

A reaction product is made by condensing a 1 molar quantity of tetrahydrofuran 2,3,4,5-tetracarboxylic dianhydride with a 2 molar portion of 2,3-dibromopropanol and 2 molar portions of glycidyl methacrylate as follows: 327.32 grams of 2,3-dibromopropanol, 0.35 grams hydroquinone and 159.25 grams of tetrahydrofuran dianhydride are charged to a 1 liter reaction flask. The mixture is heated to 120° and held for 1 hr., after which 220 grams of glycidyl methacrylate are added over a period of 1.5 hrs. such that the heat of exotherm does not permit the temperature of the reaction to exceed 135° C. After cooling to 130° C. and holding for 1 hr., the resultant resin is dissolved in 466 grams of styrene. The styrene solution can be employed in providing laminates containing antimony trioxide as described in Example 5.

TABLE I

| PHYSICAL PROPERTIES | PHYSICAL PROPERTIES OF LAMINATES EXAMPLES | | | | | | | | |
|---|---|---|---|---|---|---|---|---|---|
| | 1 | 2 | 5 | 5 | 8 | 8 | 11 | 11 | 12 |
| % Antimony Oxide (Sb$_2$O$_3$) | 0 | 5 | 0 | 5 | 0 | 5 | 0 | 5 | 0 |
| Flex Strength (psi) | 22,300 | 26,700 | 21,700 | 19,000 | 22,100 | 19,300 | 22,700 | 21,000 | 21,800 |
| Flex Modulus (psi × 10$^6$) | 1.03 | 1.17 | 1.02 | 0.95 | 0.90 | 0.84 | 1.04 | 1.04 | 1.06 |
| Barcol Hardness No. | 43–48 | 43–48 | 46–51 | 43–47 | 32–42 | 40–46 | 48.55 | 48.00 | 43.51 |
| Tensile Strength (psi) | 11,700 | 11,700 | 12,400 | 10,100 | 11,800 | 10,700 | 11,000 | 12,100 | 12,350 |
| Tensile Modulus (psi × 10$^6$) | 1.15 | 1.18 | 1.15 | 1.05 | 1.17 | 1.17 | 1.21 | 1.35 | 1.22 |
| % Elongation | 1.60 | 1.47 | 1.48 | 1.24 | 2.07 | 1.86 | 1.74 | 1.47 | 1.46 |
| Notched Izod | 12.23 | 11.50 | 11.93 | 11.91 | 11.17 | 8.69 | 10.80 | 10.91 | 12.20 |
| % Glass | 24.87 | 26.48 | 25.73 | 24.28 | 26.34 | 24.69 | 26.21 | 23.62 | 27.76 |
| G.E. Candle Test[1] | 37.9 | 46.8 | 34.9 | 46.5 | 37.00 | 47.2 | 37.00 | 42.20 | 35.30 |

[1] A.S.T.M. Test No. D-2863

From the Examples in Table I it is seen that the resins of the invention show significantly high flex strength values with and without antimony trioxide, while fire retardancy is significantly better than standard materials as indicated by the G.E. Candle Test ASTM #D2863 wherein the higher numbers indicate the better flame retardance. It is, therefore, contemplated that the resins of the invention are useful in forming castings and reinforced laminates wherein high strength and flame retardancy is required such as that used in aircraft components.

It is contemplated that the resins of the invention can be used in combination with plasticizers, antioxidants, stabilizers and the like. In addition to those used as already described, they can be used in combination with various other fillers, reinforcing filaments and fibers, pigments and coloring agents, such as glass fibers, graphite fibers, synthetic resin fibers, titanium dioxide, wood fillers, metallic fibers, mineral fibers, such as to increase the strength of molded parts, laminates and extrusions required for high temperature and fire retardant applications.

What is claimed is:

1. A polymerizable composition comprising a carbocyclic tetracarboxylic ester monomer useful for imparting flame retardance to resin polymers having the general formula:

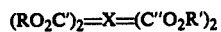

wherein =X= is selected from a tetravalent double 6 membered ring system wherein the C' carbons are attached to a pair of vicinal carbons in said ring system and the C" carbons are attached to another pair of vicinal carbons in said ring system wherein 1 each of R and R' is selected from a halogenated organic radical containing at least 2 atoms of chlorine or bromine and the other of each R and R' is selected from —H, —CH$_2$C-

H(OH)CH$_2$O$_2$CCR''=CH$_2$, and —CH[CH$_2$(OH)]CH$_2$O$_2$CCR''=CH$_2$, wherein R'' is —H or —CH$_3$; further comprising one or more ethylenically unsaturated monomers and an ethylenically unsaturated polyester resin.

2. The composition of claim 1 wherein said monomers are selected from vinyl esters, aryl vinyl compounds, vinyl nitriles, and divinyl compounds.

3. The composition of claim 1 wherein =X= is selected from naphthalene, dibenzene, benzophenone, anthracene, and dibenzylmethane.

4. A composition of claim 1 wherein said polyester resin is a condensation product of an alpha,beta-ethylenically unsaturated polycarboxylic acid and a polyhydric alcohol.

5. A composition of claim 1 wherein said tetracarboxylic ester monomer is prepared by the reaction of 1 molar portion of a dianhydride having a general formula wherein =X= is selected from a double 6 membered ring system wherein the C' carbons are attached to a pair of vicinal carbons in said ring system and the C'' carbons are attached to another pair of vicinal carbons in said ring system with 2 molar portions of a monohydroxy halogenated organic compound having at least 2 carbon atoms and at least 2 atoms of chlorine or bromine.

6. The composition of claim 5 wherein said monohydroxy compound is a di-, tri or tetra-halogenated compound selected from the group consisting of ethanol, propanol, isopropanol, butanol, isobutanol, pentanol, isopentanol, neopentanol and aromatic alcohols.

* * * * *

UNITED STATES PATENT AND TRADEMARK OFFICE
CERTIFICATE OF CORRECTION

PATENT NO. : 4,139,577
DATED : February 13, 1979
INVENTOR(S) : Erich Kuehn

It is certified that error appears in the above-identified patent and that said Letters Patent are hereby corrected as shown below:

Column 1, line 43 - U.S. Pat. No. 4,095,601 should read U.S. Pat. No. 4,093,601.

Column 1, line 53 - o should read of.

Column 2, line 34 - fist should read first.

Column 5, line 47 - condenstion should read condensation.

Signed and Sealed this

Tenth Day of July 1979

[SEAL]

Attest:

LUTRELLE F. PARKER
Attesting Officer     Acting Commissioner of Patents and Trademarks